(12) United States Patent
Nord et al.

(10) Patent No.: US 8,744,045 B2
(45) Date of Patent: Jun. 3, 2014

(54) METHOD AND SYSTEM FOR TREATING MOVING TARGET

(71) Applicant: Varian Medical Systems International AG, Zug (CH)

(72) Inventors: Janne Iimari Nord, Espoo (FI); Tuomas Erik Torsti, Espoo (FI)

(73) Assignee: Varian Medical Systems International AG, Zug (CH)

( * ) Notice: Subject to any disclaimer, the term of this patent is extended or adjusted under 35 U.S.C. 154(b) by 0 days.

(21) Appl. No.: 13/676,370

(22) Filed: Nov. 14, 2012

(65) Prior Publication Data

US 2013/0216026 A1    Aug. 22, 2013

Related U.S. Application Data

(63) Continuation of application No. 12/708,141, filed on Feb. 18, 2010, now Pat. No. 8,331,532.

(51) Int. Cl.
*A61N 5/10* (2006.01)
(52) U.S. Cl.
USPC .......................................................... 378/65
(58) Field of Classification Search
USPC .......................................................... 378/65
See application file for complete search history.

(56) References Cited

U.S. PATENT DOCUMENTS

| | | | |
|---|---|---|---|
| 4,868,843 A | 9/1989 | Nunan | |
| 5,207,223 A | 5/1993 | Adler | |
| 6,076,005 A | 6/2000 | Sontag et al. | |
| 6,118,847 A | 9/2000 | Hernandez-Guerra et al. | |
| 6,144,875 A | 11/2000 | Schweikard et al. | |
| 6,307,914 B1 | 10/2001 | Kunieda et al. | |
| 6,501,981 B1 | 12/2002 | Schweikard et al. | |
| 6,687,330 B2 | 2/2004 | Hernandez-Guerra | |
| 6,804,548 B2 * | 10/2004 | Takahashi et al. | 600/427 |
| 6,888,919 B2 | 5/2005 | Graf | |
| 7,154,991 B2 | 12/2006 | Earnst et al. | |
| 7,162,008 B2 * | 1/2007 | Earl et al. | 378/65 |
| 7,221,733 B1 | 5/2007 | Takai et al. | |
| 7,260,426 B2 | 8/2007 | Schweikard et al. | |
| 7,289,599 B2 | 10/2007 | Seppi et al. | |
| 7,302,033 B2 | 11/2007 | Carrano et al. | |
| 7,349,522 B2 | 3/2008 | Yan et al. | |
| 7,356,112 B2 | 4/2008 | Brown et al. | |

(Continued)

OTHER PUBLICATIONS

Huntzinger, Calvin, et al., "Every Breath You Take—The Image-Guided Motion Management Story", Jan.-Feb. 2003, The Journal of Oncology Management, vol. 12, No. 1, pp. 16-20.

*Primary Examiner* — Allen C. Ho
(74) *Attorney, Agent, or Firm* — Kilpatrick Townsend & Stockton LLP

(57) ABSTRACT

A method and system for providing intensity modulated radiation therapy to a moving target is disclosed. According to a preferred embodiment of the invention, a treatment plan for providing radiotherapy using a multi-leaf collimator ("MLC") comprises a plurality of sub-plans, each of which is optimized for a different phase of target movement. Movements of the treatment target are tracked in real time, and the choice of which sub-plan to implement is made in real time based on the tracked position of the target. Each of the sub-plans is preferably formulated to minimize interplay effects between target movements and MLC leaf movements, consistent with other planning goals. In addition, the sub-plans preferably include a predicted region corresponding to the next anticipated position of the target, in order to facilitate the transition to the next position.

19 Claims, 7 Drawing Sheets

(56) References Cited

U.S. PATENT DOCUMENTS

| | | |
|---|---|---|
| 7,453,983 B2 | 11/2008 | Schildkraut et al. |
| 7,453,984 B2 | 11/2008 | Chen et al. |
| 7,469,035 B2 | 12/2008 | Keall et al. |
| 7,496,173 B2 | 2/2009 | Goldman et al. |
| 7,551,717 B2 | 6/2009 | Tome et al. |
| 7,570,738 B2 | 8/2009 | Khamene et al. |
| 7,596,207 B2 | 9/2009 | Kaus et al. |
| 7,609,810 B2 | 10/2009 | Yi et al. |
| 7,623,679 B2 | 11/2009 | West et al. |
| 7,693,257 B2 | 4/2010 | Allison |
| 7,796,731 B2 | 9/2010 | Nord et al. |
| 7,835,493 B2 * | 11/2010 | Keall et al. ............... 378/65 |
| 7,835,494 B2 * | 11/2010 | Nord et al. ............... 378/65 |
| 7,894,649 B2 * | 2/2011 | Fu et al. ............... 382/128 |
| 7,961,843 B2 * | 6/2011 | Brown et al. ............... 378/65 |
| 8,073,103 B2 * | 12/2011 | Otto et al. ............... 378/65 |
| 8,229,068 B2 * | 7/2012 | Lu et al. ............... 378/65 |
| 8,295,435 B2 * | 10/2012 | Wang et al. ............... 378/65 |
| 8,295,436 B2 * | 10/2012 | Nord et al. ............... 378/65 |
| 8,331,532 B2 * | 12/2012 | Nord et al. ............... 378/65 |
| 8,467,497 B2 * | 6/2013 | Lu et al. ............... 378/65 |
| 8,503,608 B2 * | 8/2013 | Brown et al. ............... 378/65 |

* cited by examiner

METHOD AND SYSTEM FOR TREATING MOVING TARGET

CROSS-REFERENCES TO RELATED APPLICATIONS

This application claims priority to and is a continuation of U.S. Pat. No. 8,331,532, which corresponds to application Ser. No. 12/708,141 entitled "METHOD AND SYSTEM FOR TREATING MOVING TARGET" filed Feb. 18, 2010, the entire contents of which are herein incorporated by reference for all purposes.

FIELD OF THE INVENTION

The present invention is related to radiation therapy systems using multi-leaf collimators, and is particularly related to a method and system for treating moving targets.

BACKGROUND OF THE INVENTION

Radiation therapy using high intensity x-rays or particles to destroy cancerous tissue has been in use for several decades. When treating cancer, it is usually important to irradiate only a precisely defined volume conforming to the tumor, while avoiding irradiation of surrounding tissue. Multi-leaf collimators (MLCs), such as described in U.S. Pat. No. 4,868,843, issued Sep. 19, 1989, to Nunan, (the disclosure of which is incorporated by reference), have been widely adopted because they facilitate shaping of the radiation beam to conform to the site being treated, i.e., the leaves are adjusted so that the beam conforms to the shape of the tumor from the angle of irradiation. MLCs were first used to perform three-dimensional conformal radiation therapy (3D-CRT), wherein the MLC is adjusted to shape the beam to conform to the target from each treatment angle. MLCs have more recently been used to perform "Intensity Modulated Radiotherapy" (IMRT), which allows control over the radiation doses delivered to specific portions of the site being treated. In particular, IMRT allows the intensity distribution of the radiation reaching the patient to have almost any arbitrary distribution. IMRT can be implemented by iteratively positioning the leaves of the MLC, which form an aperture through which radiation is delivered, to provide desired field shapes which collectively deliver the desired dose distribution. IMRT techniques can either be static ("point and shoot" or "move and shoot"), in the sense that the leaves do not move when the beam is on or, alternatively, can be implemented by moving the leaves of the MLC continuously when the beam is on, using a "sliding window" approach. In sliding window IMRT the overall speed of leaf motion and the separation of leaf pairs are independently adjusted as the window moves, such that different portions of the treatment field are irradiated with different doses of radiation through an aperture that changes shape as it is being moved. Recently "arc therapy," wherein the system gantry moves as radiation is delivered through an MLC, has been adopted as an important mode of treatment. In arc therapy, the leaves of the MLC are adjusted as the gantry revolves around the patient.

Overall, the trend for all of these treatment techniques has been toward much greater precision in delivering a controlled dose of radiation to the target while avoiding healthy tissue. This has made it possible to deliver higher radiation doses to the target over shorter time spans. However, the ability to deliver more radiation more precisely requires the use of better techniques to ensure that the target volume is exactly in the correct position while the radiation is being delivered. Accordingly, small movements of the target have become of greater concern.

Radiation therapy is generally implemented in accordance with a treatment plan which is developed taking into account the prescribed dose of radiation to be delivered to the tumor, as well as the maximum dose of radiation which can be delivered to surrounding tissue. Treatment planning for IMRT and arc therapy is particularly challenging, and sophisticated treatment planning software and algorithms have been developed for treatement planning. Various algorithms for solving the "inverse" problem of translating the prescribed radiation doses and constraints into a delivery plan are well known. Preferably, the computer system and software used to develop the treatment plan provides an output that can be used to directly control the radiation therapy system, including the MLC leaf and gantry movements.

Typically, the desired dose prescribed in a treatment plan is delivered over several sessions, called fractions. Since the treatment volume may change between the delivery of fractions—for example, organs may shrink, swell, or change position—it is often necessary to reimage the treatment volume and to adjust the treatment plan between fractions to accommodate changes. Apart from changes that occur between fractions, tumors and surrounding tissue, including critical organs, may move while a site is being irradiated. Many of these motions occur in a substantially regular, predictable fashion, for example, as a result of normal respiratory motion.

Obtaining the desired biological response in the target region depends upon delivery of the intended fractional dose, thus achieving the planned dose distribution is critical to success of the treatment. While patients undergoing treatment are precisely positioned and immobilized according to well-known techniques, movement in the treatment field can have a significant impact on the effectiveness of a treatment plan. A treatment plan that does not take such movement into account may result too much or too little radiation reaching the intended target region and/or too much radiation reaching surrounding tissue. In the worst case scenario involving IMRT, the target may receive several times the prescribed dose when the target movement is in phase with the MLC aperture movement. On the other hand, if movement of the target region is out of phase with the MLC movement, the tumor may receive a lower than prescribed dose. In practice, interplay between the movement of the IMRT window and the treatment has been reported to generate differences of greater than 10% between the delivered and the planned dose distributions for a single fraction.

One technique for dealing with target movement is disclosed in U.S. Pat. No. 7,221,733, the disclosure of which is incorporated by reference. The '733 patent describes methods and apparatuses for tracking movement of the target and adjusting and/or gating the beam to account for target movements. Gating refers to turning the beam off in response to target movement so that healthly tissue is not irradiated. Another approach to dealing with target movement is disclosed in recently filed and co-assigned U.S. patent application Ser. No. 12/196,639, now U.S. Pat. No. 7,796,731, the disclosure of which is also incorporated by reference. This application teaches techniques for developing treatment plans using leaf sequences that minimize the effects of target movement. Plans made in accordance with the teachings of the '639 application are more robust insofar as they are less sensitive to target movements. There is a continued need, however, for improved techniques for dealing with the moving target problem, as described herein.

SUMMARY OF THE INVENTION

The present invention provides a method of performing intensity modulated radiotherapy (IMRT) for a target region that moves along a path or trajectory.

In one aspect the present invention involves a method of using a radiation therapy system having a multileaf collimator to perform intensity modulated radiation therapy on a selected target volume within a patient, wherein the target volume comprises substantially predictable movements, comprising, delivering radiation in accordance with a treatment plan developed for said patient, wherein the treatment plan is developed using a plurality of inputs and constraints including anticipated target volume movements and the interplay between movements of the multileaf collimator and said target movements, tracking movement of the target volume in real time to determine the target volume position while delivering radiation to the patient, and moving leaves of said multileaf collimator in real time to adjust for target volume movement. Preferably, the treatment plan comprises a plurality of sub-plans, at least some of which correspond to anticipated phases of the target movement, and the method further comprises selecting a sub-plan to implement based on the tracked target position. More preferably at least one of said sub-plans includes as one input a prediction region corresponding to the next anticipated target volume position such that the sub-plan facilitates the transition of the MLC leaves from one target position to the next anticipated position; and the method includes moving the leaves of said MLC based the sub-plan corresponding to a first target volume position, before implementing a second sub-plan corresponding to a second target volume position.

In another aspect the present invention is directed to a method of developing a treatment plan for using a radiation therapy system to irradiate a moving treatment volume through a multileaf collimator, comprising, incorporating data concerning a prescribed dose of radiation to be delivered to a target volume within said treatment volume, incorporating data concerning constraints on the amount of radiation permitted to be delivered to areas within the treatment volume outside of the target volume, incorporating data concerning a plurality of target positions corresponding to movement of the target, and iteratively developing a treatment plan comprising a plurality of sub-plans corresponding to different target positions, where each of said sub-plans is based on said prescribed dose data, said constraint data, said target movement data, and on interplay effects between target movements and movements of the leaves of said multileaf collimator. Preferably, at least one treatment sub-plan is also based on the next predicted position of the target. The treatment plan may be for IMRT or for arc therapy. The treatment plan is preferably based on the machine parameters for the radiotherapy system that will be used to implement the plan and the treatment plan includes machine readable instructions for operating the radiotherapy system.

In another aspect the invention is directed to a method of using a radiation therapy system having a multileaf collimator to irradiate a selected target volume within a patient wherein the selected target volume moves in a substantially known manner, comprising developing a treatment plan for irradiating a moving treatment volume through a multileaf collimator, wherein the treatment plan is developed by incorporating data concerning a prescribed dose of radiation to be delivered to a target volume within said treatment volume, incorporating data concerning constraints on the amount of radiation permitted to be delivered to areas within the treatment volume outside of the target volume, and incorporating data concerning a plurality of target positions corresponding to knowns movements of the target volume, and then iteratively calculating a treatment plan comprising a plurality of sub-plans corresponding to a plurality of target positions, where the sub-plans are formulated taking into account the prescribed dose data, the constraint data, the position data, and interplay effects between said position data and movements of the leaves of said multileaf collimator. The method further involves tracking movement of the target volume in real time to determine the target volume position, and implementing a selected one of said sub-plans in real time based on the position of the target volume. Preferably, at least some of said sub-plans incorporates data concerning the next predicted position of the target volume in order to facilitate the transition of said leaves from one target volume position to the next anticipated target volume position. The radiation therapy system may have a rotatable gantry which houses the radiation source, which is rotated while radiation is being delivered to the patient.

In yet another aspect, the present invention is directed to a computer readable medium comprising one or more algorithms stored thereon for radiotherapy treatment planning, wherein the algorithms implement the following steps in connection with developing a patient treatment plan for use with a radiotherapy treatment system having a multileaf collimator: accepting data concerning a prescribed dose of radiation to be delivered to a target volume within a treatment volume, accepting data concerning constraints on the amount of radiation permitted to be delivered to areas within the treatment volume outside of the target volume, accepting data concerning a plurality of target positions corresponding to movement of the target, for at least one of said plurality of target positions, establishing a predicted region corresponding to the next antipated phase of target movement, iteratively developing a treatment plan comprising a plurality of sub-plans corresponding to different target positions, where each of said sub-plans is based on said prescribed dose data, said constraint data, said target movement data, said predicted region and on interplay effects between target movements and movements of the leaves of multileaf collimator.

DETAILED DESCRIPTION

Figure 1:
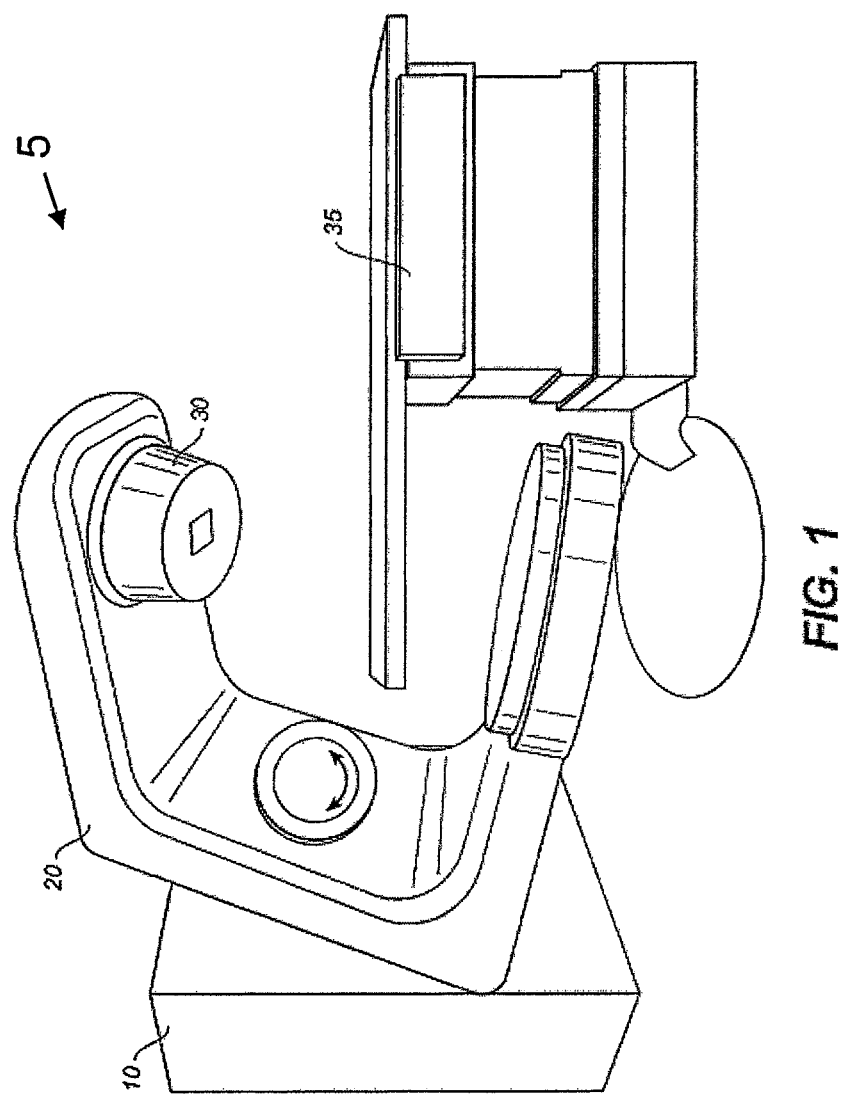
FIG. 1 is an isometric view of an exemplary radiation therapy system.
Figure 2:
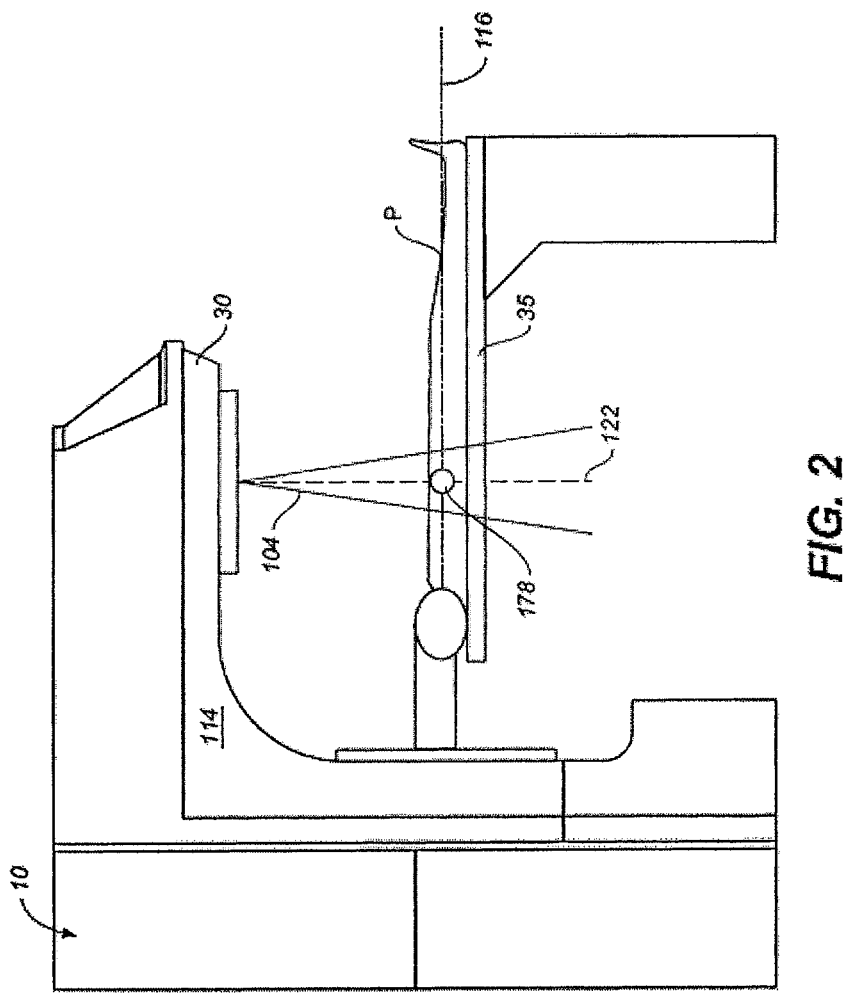
FIG. 2 is an elevation view of an exemplary radiation therapy system.

FIGS. 1 and 2 depict an exemplary radiation therapy system 5 of the type which is useful in practicing the present invention. Referring to FIG. 1, a perspective view of radiation therapy system 5 (sometimes referred to as a linear accelerator) is shown. Typically, such a system is be capable of generating either an electron (particle) beam or a high energy x-ray (photon) beam for use in radiotherapy treatment of patients on a treatment table 35. While high energy x-rays are predominantly used for radiation therapy, high energy particles, such as electrons and protons, are also sometimes used. Systems for generating proton beams are typically different than systems for generating x-rays or electron beams, however, such differences are not pertinent to a discussion of the present invention. Accordingly, as used herein the term radiation therapy is intended to encompass all such techniques, and the present invention has application to all such techniques. Thus, when reference is made herein to x-rays or radiation, such terms should be also understood to encompass use of high energy particles. For purposes of the present discussion, only x-ray irradiation will be discussed.

Stand 10 supports a rotatable gantry 20 with a treatment head 30. A control unit (not shown), housing the operational electronics for controlling the system is coupled to the system. A high voltage source is provided within the stand or in the gantry to supply voltage to an electron gun (not shown) positioned on an accelerator guide located in gantry 20. Electrons emitted from the electron gun enter into the guide (not shown) where they are accelerated to a high energy by an RF (microwave) source used to generate an electromagnetic field within the waveguide. Specifically, electrons are accelerated in the waveguide by the electromagnetic field, exiting the waveguide as a high energy electron beam, typically at megavolt energies. The emergent electron beam strikes a suitable metal target, emitting x-rays in the forward direction in a substantially conical pattern.

Referring now to FIG. 2, a somewhat more detailed side view of a radiation therapy system of the type which may be used in connection with the present invention is shown. A patient P is shown lying on treatment table 35. X-rays formed as described above are emitted from the target in treatment head 30 in a divergent beam 104. Typically, a patient plane 116, which is perpendicular to the page in FIG. 2, is positioned about one meter from the x-ray source or target, and the axis of gantry 114 is located on plane 116, such that the distance between the target and isocenter 178 remains constant when gantry 114 is rotated. Isocenter 178 is at the intersection between patient plane 116 and central axis 122 of beam 104. A treatment volume to be irradiated is located about the isocenter. As used herein the entire volume which received radiation during therapy is sometimes referred to as the treatment volume, and the tissue being treated (e.g., a tumor), is sometimes referred to as the target volume or, simply, the target. Thus, the target volume falls within the treatment volume.

X-ray collimators comprising an x-ray blocking material (not shown), commonly referred to as "jaws", are positioned in treatment head 30 to define the maximum dimensions of the x-ray beam at the patient plane. Typically, the jaws are moveable and, when fully open, define a maximum beam of about 40 cm×40 cm at patient plane 116. A multileaf collimator ("MLC") (not shown in FIG. 2) is positioned at the exit of treatment head 30, to further shape the x-ray beam. Since its introduction in 1990 the MLC has become a standard feature of most radiation therapy systems. MLCs sold by Varian Medical Systems Inc. (affiliated with the assignee of the present invention) use up to 120 individually controllable leaves, typically thin slices of tungsten, that can be moved into or out of the x-ray beam under the control of system software. The MLC can be rotated, moved and configured to collimate the x-rays to provide conformal treatment of tumors from various angles ("3D conformal,") as well as intensity modulated radiotherapy ("IMRT"), whereby different radiation doses are delivered to different portions of the treatment area from any given angle. The treatment volume, i.e., the irradiated volume proximate to the isocenter in the path of the x-ray beam, is defined by the jaws, the angle of the treatment head and the MLC. In IMRT the leaves of the MLC are moved, such that the treatment volume comprises the total volume exposed during the course of a treatment.

While not shown in FIG. 1 or 2, modern radiation therapy systems often also include an imaging subsystem, typically a low energy x-ray CT system, that allows the system operator to obtain and view internal images of the patient. This facilitates precise positioning and alignment of the tumor or other target volume and can be used in real time to track movements of the target volume and of the larger treatment volume. Exemplary radiation therapy systems comprising CT imaging subsystems are described in U.S. Pat. No. 6,888,919, the disclosure of which is incorporated by reference.

Radiation therapy treatment planning begins with precise imaging of the target volume and surrounding tissue. The images are used to identify the spatial extent and boundaries of the target and nearby structures, such as critical organs, in treatment volume. In accordance with an aspect of the present invention, where the target or other portion of the treatment volume is in motion, (e.g., due to respiration), pre-planning imaging may be used to map phases and trajectory of the normal target motion. The imaging information is then used in the development of a treatment plan for delivering a prescribed dose of radiation to a tumor or other target volume while minimizing the dose of radiation delivered to surrounding tissue. Where there are one or more sensitive organs in the treatment volume, specific constraints may be incorporated to limit the acceptable dose of radiation they each receive. Generally speaking, a treatment plan comprises, at a minimum, adjusting the MLC and irradiating one or more selected portions of the treatment volume. In many, if not most, instances, a treatment plan often involves irradiating the treatment volume from a plurality of different angles, with the MLC aperature being adjusted, as necessary, for each angle. Various treatment planning software and other tools are available for developing specific treatment plans are know. Accordingly, many of the details of the various techniques for creating such plans are not described herein.

Generally, techniques for developing treatment plans for conformal radiation, IMRT or are therapy are directed to solving the "inverse" problem of determining the optimal combination of angles, fluences, doses and MLC leaf movements to deliver the desired total radiation dose to the target volume while minimizing irradiation of healthy tissue. This inverse problem becomes very complex for developing arc therapy plans where the gantry is in motion while the target volume is irradiated. Heretofore, radiation oncologists or other medical professionals, such as medical physicists and dosimetrists, have used a variety of available treatment planning optimization algorithms to develop and optimize treatment plans. Typically, as described above, such planning starts with volumetric information about the target tumor and about any nearby tissue structures obtained by imaging. For example, such information may comprise a map of the planning target volume ("PTV"), such as a prostate tumor, that is prescribed by the physician to receive a therapeutic radiation dose with allowable tolerances. Volumetric information about nearby healthy tissue may include for example, maps of the patient's bladder, spinal cord and rectum, each of which may be deemed an organ at risk that can only safely receive a much lower dose of radiation without risk of damage.

This volumetric information along with the prescribed doses and dose limits, and similar objectives set by the medical professionals, become the basis for calculating the treatment plan, including an optimized dose distribution. This may for example, be reduced to an objective function or a single figure of merit that accounts for the relative importance of various trade-offs inherent in such a plan along with constraints that must be met for the plan to be medically acceptable or physically possible. Moreover, to create a deliverable treatment plan, treatment planning algorithms must also account for the capabilities and limitations of the specific radiation therapy system that will be used for treating the patient. These will include, for example, the type, energy level(s) and fluence of the radiation beam, and the capabilities of the MLC.

Generally speaking, treatment planning algorithms proceed by calculating the radiation dose received by each voxel in the treatment volume, adjusting one or more variable system parameters, such as the angle of irradiation or the positions of the MLC leaves, and then recalculating the dose received by each voxel. This process is ideally performed iteratively until an optimized plan is reached. However, the amount of time needed to perform the large number of calculations for each iteration places a practical limit on the number of iterations that can be performed. Accordingly, in practice the optimization routine is terminated after a predetermined amount of time, after a predetermined number of iterations, or after some other practical limit is reached. Generally speaking, there is a trade-off between the accuracy and speed of the different algorithms available for treatment planning.

Generally two types of algorithms are used in treatment planning: (1) dose calculation algorithms based on a given set system parameters, e.g., gantry angle, MLC leaf positions, etc., and (2) search algorithms which use various techniques to adjust system parameters between dose calculations to achieve optimization of the plan. Known dose calculation algorithms include various Monte Carlo ("MC") techniques, pencil beam convolution ("PBC"), generalized Gaussian pencil beam ("GGPB"), collapsed cone convolution ("CCC"), and anisotropic analytical algorithm ("AAA"). Known search algorithms include various stochastic and deterministic methods, including various simulated annealing ("SA") techniques, algebraic inverse treatment planning ("AITP"), simultaneous iterative inverse treatment planning ("SIITP"), iterative least-square inverse treatment planning ("ILSITP"), and superposition convolution ("SC"). Such techniques are known in the art, and each of the techniques has advantages and disadvantages relative to the others. For example, stochastic dose calculation methods, such as Monte Carlo techniques, are more accurate, but typically require more time to perform. Each of the methods requires iterative dose calculations for optimization, and generally a high number of dose calculation iterations or "passes" are required to converge on an optimal plan. Typically, each iteration involves changing the boundary conditions using the search algorithm and recalculating the dose distribution.

The treatment plan prescribes the fluence each portion of treatment volume should receive from each angle. From any given angle there are many leaf sequences (i.e., many combinations of leaf movements) that can be used to produce a given fluence. Moreover, treatment plans typically provide for irradiating the target from multiple angles or, in arc therapy, while the gantry is moving. Most treatment planning has proceeded on the basis that the treatment volume is stationary while the patient is being irradiated, i.e., target motion was not taken into consideration in developing the treatment plan. Thus, prior art treatment planning generally made no effort to optimize leaf movements in relation to target motion. As discussed above, the present invention is directed to the problem which arises when the treatment volume moves while being irradiated.

Again, generally speaking, after a treatment plan is created it is implemented, in part, by controlling the angle of incidence and the leaves of the MLC to allow the desired radiation dose to reach the selected portions of the treatment volume from the selected angles. In the simplest type of treatment plan, the MLC is adjusted to provide static conformal irradiation of a specific site from a single angle. In IMRT plans, the leaves are moved into different positions between or during irradiations from at least one angle. In arc therapy, the treatment plan involves moving the gantry while simultaneously adjusting the leaves of the MLC. As used herein, moving the leaves of the MLC includes rotating the axis of the MLC.

As noted, the treatment volume often moves in a predictable way, in other words its motion may be substantially periodic and substantially conform to a determinable trajectory. These predictable movements can be mapped using imaging as described above. FIGS. 3A-3D show "snapshots" at different points in time of a portion of a target portion 4 that moves along a substantially regular trajectory. These figures also show the radiation beam 8 reaching the patient through an IMRT sliding window. Moving target portion 4 travels along a trajectory (as illustrated by the arrows) in a substantially periodic manner. Such motion may be caused, for example, by respiration. Target portion 4 may be thought of as representing a portion of a tumor which is prescribed to receive a certain fractional dose of radiation. Area 2 comprises the entire area defined by movement of target portion 4, and includes, at any point in time, both target portion 4 and other tissue, for example, a different portion of the tumor for which a different fractional dose is prescribed.

Figure 3A:
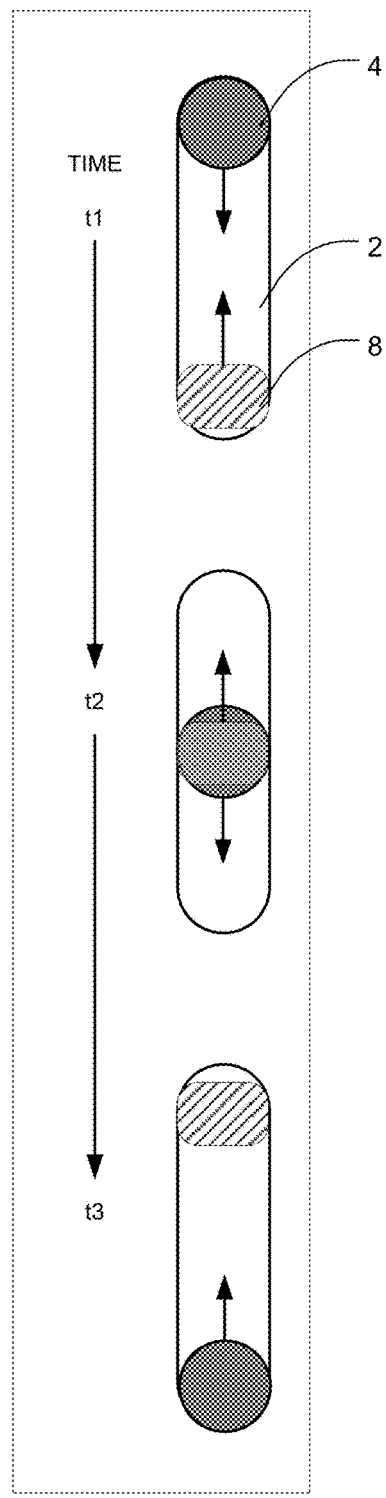
FIGS. 3A-3D depict the relationship between a moving target and a sliding IMRT window at different points in time.
Figure 3B:
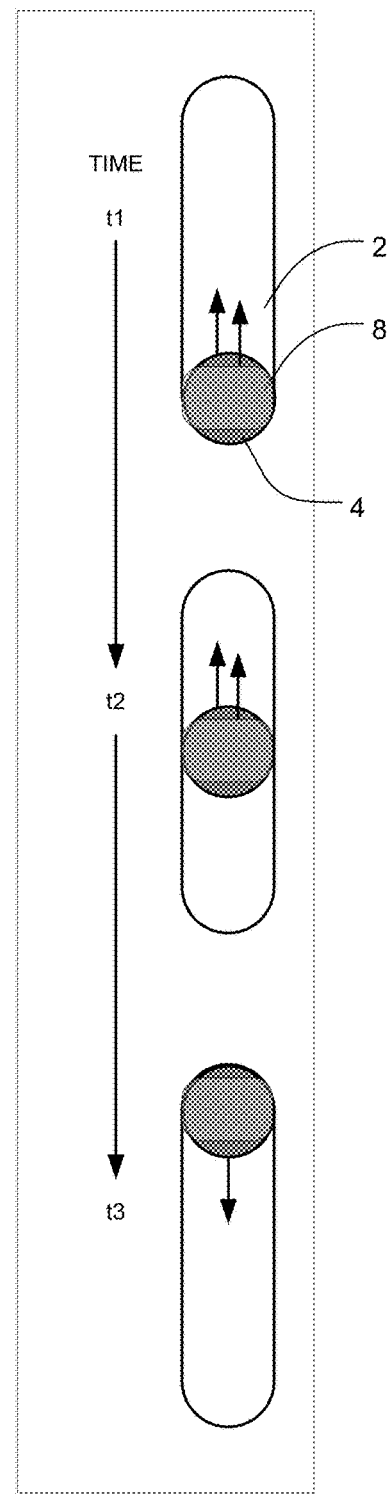

Each of FIGS. 3A-3D show the relationship between the target portion 4 position and the incident radiation 8 through the sliding IMRT window at three points in time (t1, t2, t3). In each instance geometric area 2 receives the same overall dose of radiation during the time t1 to t3; however, because of target portion motion, the patient volume irradiated during the time t1 to t3 does not necessarily correspond to geometric area 2. For demonstrative purposes FIGS. 3A and 3B depict target portion 4 and the IMRT window 8 moving at substantially the same rate in parallel paths. In FIG. 3A, the motion of target portion 4 and radiation through IMRT window 8 are out of phase, such that they overlap only briefly at t2. In FIG. 3B, the motion of target portion 4 and radiation through IMRT window 8 are in phase, such that they overlap throughout the time radiation through the IMRT window 8 moves through area 2. It can be seen that in these examples, where movement of the sliding window 8 and the target portion 4 are in the same direction, the movements interplay and can have a major impact on the delivery of the proper amount of radiation to target portion 4. Specifically, when window movement and target portion movement are in phase, the target portion can get too much radiation, but when they are out of phase, it can get too little. FIGS. 3A and 3B exaggerate the interplay effect due to the fact that the target portion 4 and beam 8 move at substantially the same speed. However, they demonstrate the problem and show that the phase, i.e., the starting position and direction of the target portion 4 relative to the beam 8, can be important. Those skilled in the art will understand that the problem of interplay effects due to target portion motion will cause unoptimized results in other circumstances.

Figure 3C:
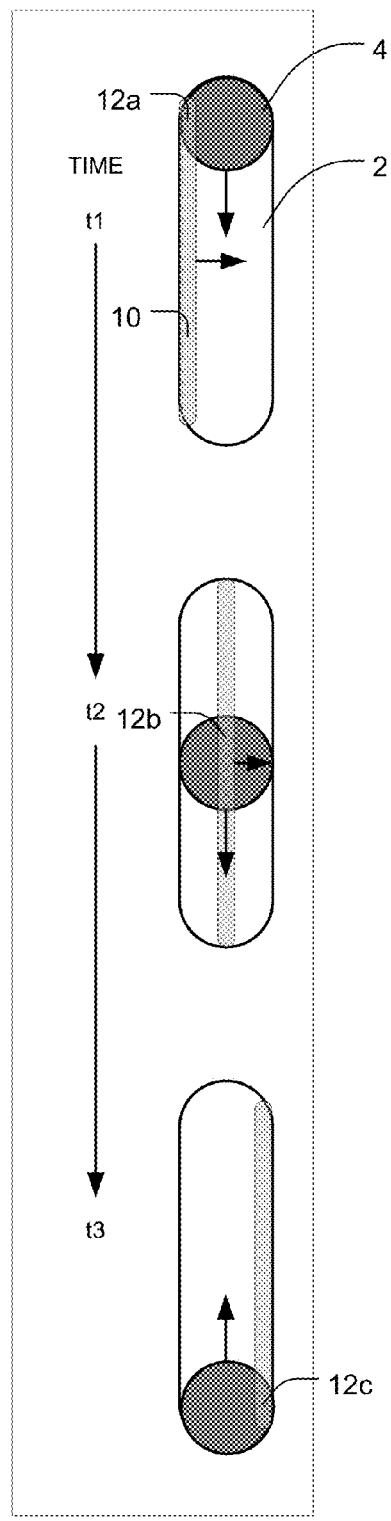
Figure 3D:
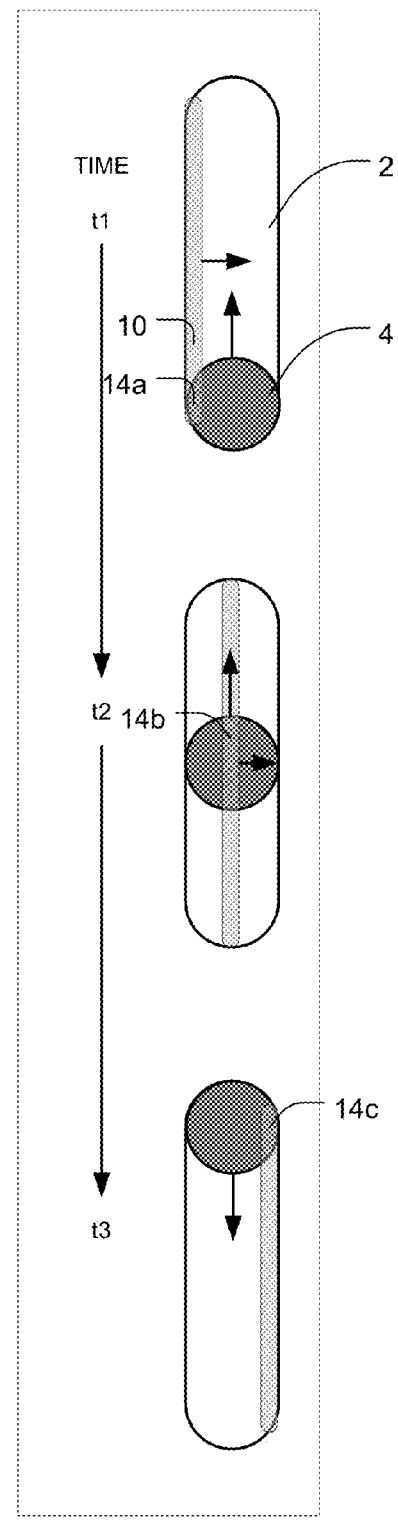

In contrast, in FIGS. 3C and 3D the IMRT sliding window 10 moves orthogonally to the trajectory of target portion 4 from a first position 12a, 14a at a first time point t1, to a second position 12b, 14b at a second time point t2, and to a third position 12c, 14c at a third time point t3. As depicted, in this orientation the IMRT apertures are generally longer in the direction of target movement, and preferably extend substantially the length of area 2. As depicted FIGS. 3C and 3D, the amount of radiation delivered to the target portion 4 is relatively unaffected by target portion motion or the phase of the motion relative to the IMRT window. Thus, the interplay effect is minimized.

Figure 4:
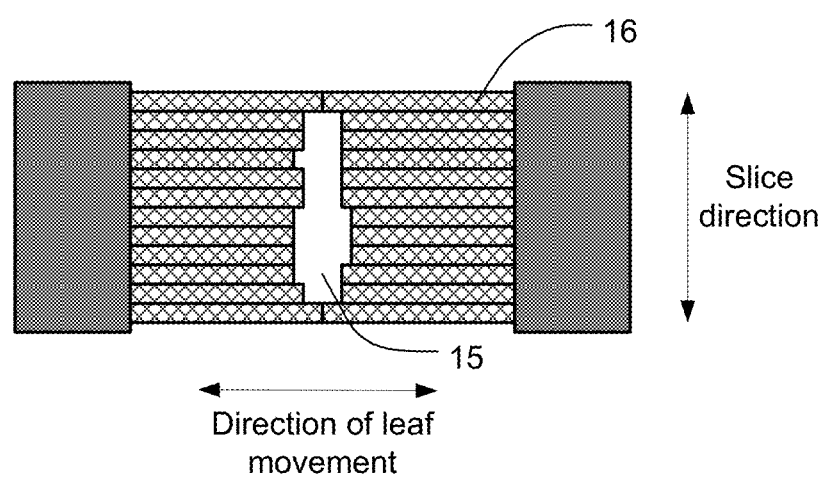
FIG. 4 is a representation of an MLC showing the leaves forming an aperture.

FIG. 4 shows an exemplary MLC plane having a plurality of leaves 16, arranged in opposing pairs, and an aperture 15 created by selected leaf movements. Radiation passes through and is shaped by the aperture 15 to create a beam. In IMRT, aperture 15 is moved continuously (sliding window) or periodically (point and shoot) across the face of the MLC in either of the directions indicated in FIG. 4. As aperture 15 is moved its shape may be adjusted to control the fluence to different portions of the treatment volume, i.e., the combined leaf movements may be used, in known fashion, to vary the fluence delivered to different portions of the treatment volume. One embodiment of the present invention uses leaf sequences wherein the MLC aperture is elongate in a direction that is generally parallel to the motion of target portion 4 and substantially equal to the length of region 2, as shown in FIGS. 3C and 3D, to minimize the interplay effect. To form an appropriate MLC aperature parallel to the target portion's movement, the leaves may most easily be oriented to move perpendicularly to that movement, but other orientations are possible. The leaves need not be oriented in the same direction as the movement of the aperture, although such orientation may simplify planning.

Having the IMRT window (and hence the leaf) movement perpendicular to the target portion movement can be used to minimize interplay effects as described. However, determining the orientation of the leaves also involves consideration of other factors, for example, the shapes of the apertures necessary to properly treat the tumor. Specifically, some shapes present greater difficulties and can only be formed by a limited number of leaf arrangements. Thus, in some cases there is a trade-off between reducing interplay effects and forming the apertures for treatment.

Optimization of leaf movements may also involve controlling the time each slice of the target portion is exposed to radiation through the MLC aperture. For example, if each slice intersects with the open aperture for about the duration of one movement cycle, the dose distribution will be closer to the planned average distribution. A variable dose rate could be used to better control the exposure time for groups of slices. While timing the dose in this way is effective in conjunction with the present invention, and timing or gating in general is useful in a variety of applications, timing alone is not sufficient to avoid interplay effects in an un-optimized system. Due to the periodic nature of the target portion movement and the difficulties in determining the precise location of the target portion 4 within region 2 at any given time, it is not practical to attempt to avoid phase problems, such as the overlapping situation shown in FIG. 3B, by simply timing the dose.

While FIGS. 3A-3D depict a linear target trajectory, in the more general case the trajectory of the target may be non-linear. When the trajectory has some other shape, such as a curve, additional considerations must be taken into account in order to determine the proper orientation for the aperture and the related optimized leaf sequence. The best technique for handling a non-linear trajectory will depend on the exact shape and other aspects of the system, such as the physical constraints on leaf movement. In some cases, it may be sufficiently accurate and most efficient to simply map the trajectory to a predominant direction—a major axis of the trajectory curve, for example. In other cases, a rigid translation can be used to reduce the trajectories to a single direction, again, such as a predominant direction. This approach might be particularly useful for multiple, non-linear trajectories. Where the trajectory is more complex, it can be obtained from deformable image registration, in which imaging is used to find a best fit. There, features of the target portion are matched in order to align the trajectory with a template image. With other complex trajectories, a point-specific movement model might be used to identify the trajectory, such as the use of boundary conditions to model the target portion. Once the trajectory has been obtained, if necessary, the trajectory can be mapped or translated into a predominant direction as discussed above.

As noted above, there may be overriding considerations that make it necessary to give secondary importance to orienting the MLC to minimize the interplay between target motion and leaf movements. Nonetheless, in accordance with an aspect of the present invention, the angle between the window formed in the MLC and the target trajectory is preferably optimized to the extent possible during treatment planning to minimize the interplay between the two. Preferred methods for formulating robust treatment plans are described in the aforementioned, coassigned U.S. patent application Ser. No. 12/196,639, now U.S. Pat. No. 7,796,731, the disclosure of which is incorporated by reference. However, in one aspect the present invention embraces any method of obtaining a treatment plan that reduces interplay effects and is not meant to be limited to the methods described in the '639 application.

In some cases, a treatment plan in accordance with the foregoing teachings produces a fluence that has the same value at all positions where it is possible for the tumor to be. For example, in FIGS. 3C and 3D, a vertical slice of the area 2 is always being irradiated although target portion 4 only occupies a portion of area 2 at any given time. Thus, the fluence may result in unnecessary irradiation of some portions of region 2, including healthy tissue. (In this regard, it should be noted that unnecessary irradiation of portions of region 2 also occurs using the un-optimized system unless movements of target portion and the IMRT window 8 are exactly in phase as shown in FIG. 3A.) Accordingly, further improvements to reduce the unnecessary radiation delivered to regions in the trajectory of the target portion would be beneficial.

One solution to the moving target problem has been to track the moving tumor and to adjust leaf positions in real time and/or to gate the beam on and off. Tracking is feasible for regular slow movements, such as those associated with respiration. For example, the typical respiration cycle takes a few seconds and generally involves relatively small movements, such that appropriate MLC leaf movements can be made in real time. (In this connection it is noted that patients can generally comply with simple instructions concerning how to breathe while being treated.) In addition, tracking can involve moving the patient couch and/or gantry to offset patient movements. On the other hand, while gating is generally undesirable, it can be used when there are sudden, unexpected patient movements. Again, applicants refer to U.S. Pat. No. 7,221,733, which discloses a system and method for tracking target movements. In addition, the '733 patent discloses that tracking signals can be superimposed on a treatment plan to control leaf movements. However, it is very difficult to do the calculations needed to adjust the treatment plan in real time to account for changes in the target volume position, especially in the case of IMRT. The '733 patent further discloses breaking the target movement into a plurality of phases and calculating a separate IMRT plan for each phase of the breathing cycle.

In accordance with an aspect of the present invention, an IMRT sub-plan that is calculated for each phase of a target's movement and each sub-plan is developed to minimize interplay effects consistent with other constraints. Preferably, the plurality of sub-plans are simultaneously optimized by the treatment planning software, and are optimized using constraints from all of the phases. Note that the fluences should normally be the same for each phase of target position. The optimization process, in addition to taking into account the target region and forbidden regions for each phase, preferably includes a third region comprising the predicted area of the next phase, (the "predicted region"). Inclusion of the predicted region in the optimization process allows the treatment planning software to not only optimize for the specific phase, but to do so in a way that puts the leaves in position to be ready for the next phase. Moreover, a predicted region can be used to develop a plan that instructs the system to begin leaf movements for the next phase in advance. The predicted region is derived from the phase information described above, i.e., it can be empirically established by imaging or otherwise recording the patient's movements over a plurality of cycles.

As noted, the optimization software may optimize the fluences simultaneously to multiple phases. According to an aspect of the present invention, one method to optimize to multiple phases is to calculate two doses for each phase—a first dose which is the maximum dose that can be delivered, assuming fluence is delivered to all regions, including non-target regions, that are not forbidden, and a second dose which is the minimum dose that can be delivered to the target region. Using a value less than the maximum permissible dose may facilitate the transitioning of the MLC leaves to the predicted region. Thus, both doses are considered when optimizing the plan for the predicted region, i.e., in preparing for the subsequent phase of motion.

The method of the present invention does not require intense calculations during delivery. Thus, the technique may be implemented using currently available computer technology without concern for delays caused by processing. In the event that unanticipated patient movement would cause the beam to irradiate a forbidden region or cause a failure to irradiate the target region, the beam is gated off until the MLC leaves and patient are returned to the correct position relative to each other.

Thus, in accordance with an embodiment of the present invention, a radiation therapy system is used to perform IMRT on a patient treatment volume in accordance with a treatment plan that is developed to minimize interplay effects and to account for predictable patient movements. As the plan is implemented, i.e., as the patient is irradiated, the movements of the target volume are monitored or tracked in real time and MLC leaf movements are adjusted in real time based on said monitoring. The treatment plan takes into account normal treatment planning constraints, such as the prescribed dose to be delivered to the tumor, the maximum dose that can be tolerated by the surrounding tissue, and machine capabilities. In addition, the treatment plan is developed, consistent with these constraints, to minimize interplay effects and, preferably, to anticipate patient movements such that the MLC leaves are favorably positioned to move to the next movement phase. Preferably, the treatment plan comprises a plurality of sub-plans corresponding to anticipated phases of patient movement, such that the particular sub-plan that is implemented at a given time corresponds to the target position, as measured in real time.

In a further aspect of the present invention, a computer system comprising treatment planning software is used for developing the treatment plan, and the treatment planning software is stored on a machine readable media such as a memory device. Preferably, the computer system and software outputs a treatment plan that includes machine controls used to directly operate the radiation therapy system that is used to implement the plan.

Figure 5:
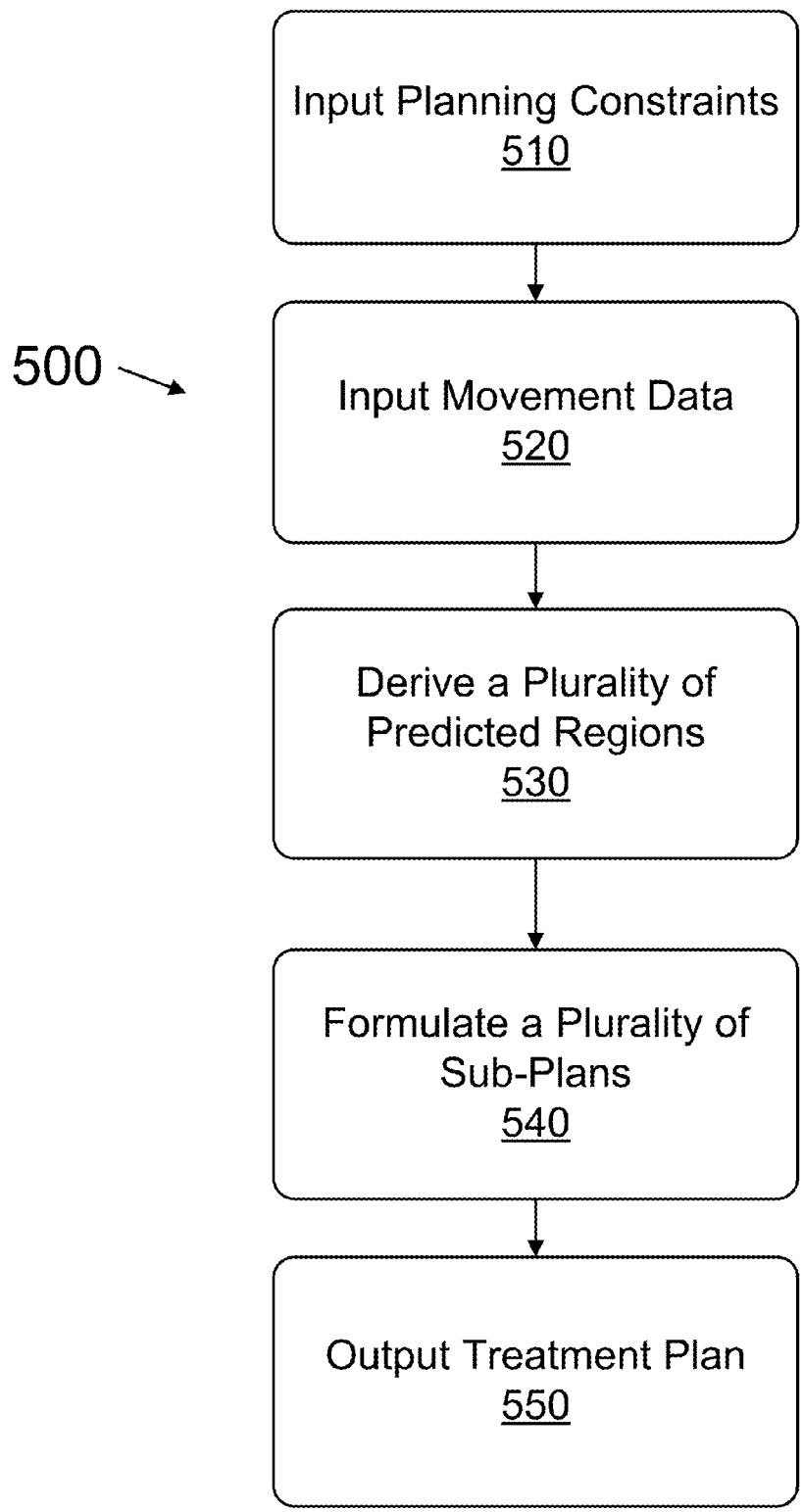
FIG. 5 is a flow chart showing steps for developing a treatment plan in accordance with an embodiment of the present invention.

FIG. 5 is a flow chart 500 showing the principle steps for developing a treatment plan in accordance with an embodiment of the present invention. As noted the treatment plan is developed using planning software operated on a computer system. The software, comprising the necessary algorithms for developing the plan, is stored on a computer readable medium. For convenience the combination of computer hardware (including peripheral devices, such as devices for inputting, displaying and outputting data) and planning software will be referred to as the treatment planning system. The treatment planning system may optionally be adapted to communicate directly with the radiotherapy system to implement the plan after it has been developed.

At step 510 planning contraints are loaded or inputted. Such constraints include both empirically derived constraints and system constraints. They may include, for example, volumetric data for the tissue structures in the treatement volume (e.g., the shape of the tumor and any organs at risk), prescribed dose data for the target volume, dose limit data for healthy tissue, (e.g., organs at risk), and data concerning system limitations (e.g., fluence capabilities, MLC parameters, gantry speed, table movement, etc.).

Next, at step 520, empirically obtained periodic movement data is loaded or inputted into the treatment planning system. Preferably, the movement data comprises three-dimensional information about the position of the target volume and the treatment volume at a plurality of different positions or phases associated with a repetitive motion, such as respiration. Based on the movement data, the software then, at step 530, associates a "predicted region" with each position or phase, the predicted region being the next anticipated position of the treatment volume when it moves to the subsequent phase. Thus, if the movement data comprises six phases in the following sequence, P1>P2>P3>P4>P5>P6>P1 . . . , then P6 is the predicted region for P5 and P1 is the predicted region for position P6. (Note that two different phases may reflect the same physical position, but different directions of movement.)

At step 540 the treatment planning system formulates a plurality of sub-plans for the treatment plan. Preferably, a sub-plan is formulated for each phase entered at step 520. Each sub-plan may be developed using standard treatment planning techniques (e.g., iteratively using a combination of one or more dose calculation algorithms and one or more search algorithms) including those described above. However, in addition to the normal parameters used in formulating a treatment plan (e.g., prescribed doses and treatment volume and system constraints), according to the preferred embodiment of the present invention, each sub-plan is also based on and reflects the data about the predicted region. At least one and preferably all of the sub-plans are optimized to facilitate leaf movements to the predicted region. In other words, the plan seeks to find the MLC leaf positions in a given phase that not only meet the needs of that phase, but which also make it easy to transition the leaves into the anticipated position for the next phase (i.e., the predicted region). Further, each sub-plan preferably seeks to minimize interplay effects, consistent with other planning parameters.

In accordance with a further aspect of the present invention, the process of developing sub-plans calculates two doses for each phase. The first dose is the maximum dose that can be delivered to the entire treatment volume other than any portion of the region that is designated as a "forbidden region." (A forbidden region may correspond to an organ at risk.) The second dose is the minimum dose that needs to be delivered to the target volume to ensure a therapeutically effective dose of radiation to the target. The calculation of two doses in this manner facilitates the use of the predicted region because it allows radiation to be delivered based on anticipated movements. For example, referring to FIGS. 3C and 3D, it is seen that radiation is delivered both to the target and to the surrounding tissue during each phase, and the calculation of two doses for each phase facilitates planning for this. Normally, the higher of the two doses will be used, but in some instances, a lower dose will better enable the transition from one phase to the next. While reference has been made to a "forbidden region" (which is believed to be the most practical approach), the concept should be considered include a region in the treatment volume that is not absolutely forbidden but, rather, is substantially constrained.

As noted, according to a preferred embodiment of the present invention, each sub-plan developed at step 540 also addresses interplay effects. At least one and preferably all of the sub-plans are optimized to minimize interplay effects between MLC leaf movements and treatement volume movement, as described above. As used herein, the term "optimized" is not intended to mean or require that the sub-plan be fully optimized or that the parameter being "optimized" is given greater weight than other planning parameters. As noted, optimization is an iterative process and there is typically a practical limit to the number of iterations that can be performed in developing a treatment plan. Moreover, as noted, a treatment plan may involve competing goals; for example, one goal may be to deliver a prescribed dose to a tumor, and another goal may be to minimize interplay effects. These goals may be given different weights; for example, achieving the correct dose to the tumor may be given more weight than reducing interplay effects. Thus, as used herein, a plan may be optimized for a particular parameter or goal even though the treatment planning system does only a finite number of iterations (i.e., additional iterations might further improve the plan), and even though optimizing the parameter is given a lower weight or importance than optimizing another parameter.

Finally, after the treatment plan, comprising a plurality of sub-plans, is completed the plan is outputted from the system at step 550. Preferably, the treatment planning system can directly communicate machine readable instructions or controls to the radiotherapy system such that the plan can be implemented automatically by the treatment system. For example, the ECLIPSE™ treatment planning system offered by Varian Medical Systems, Inc., provides this capability. Alternatively, the treatment plan can be outputted in any other suitable form, including, be stored in electronic form on a computer readable medium.

Figure 6:
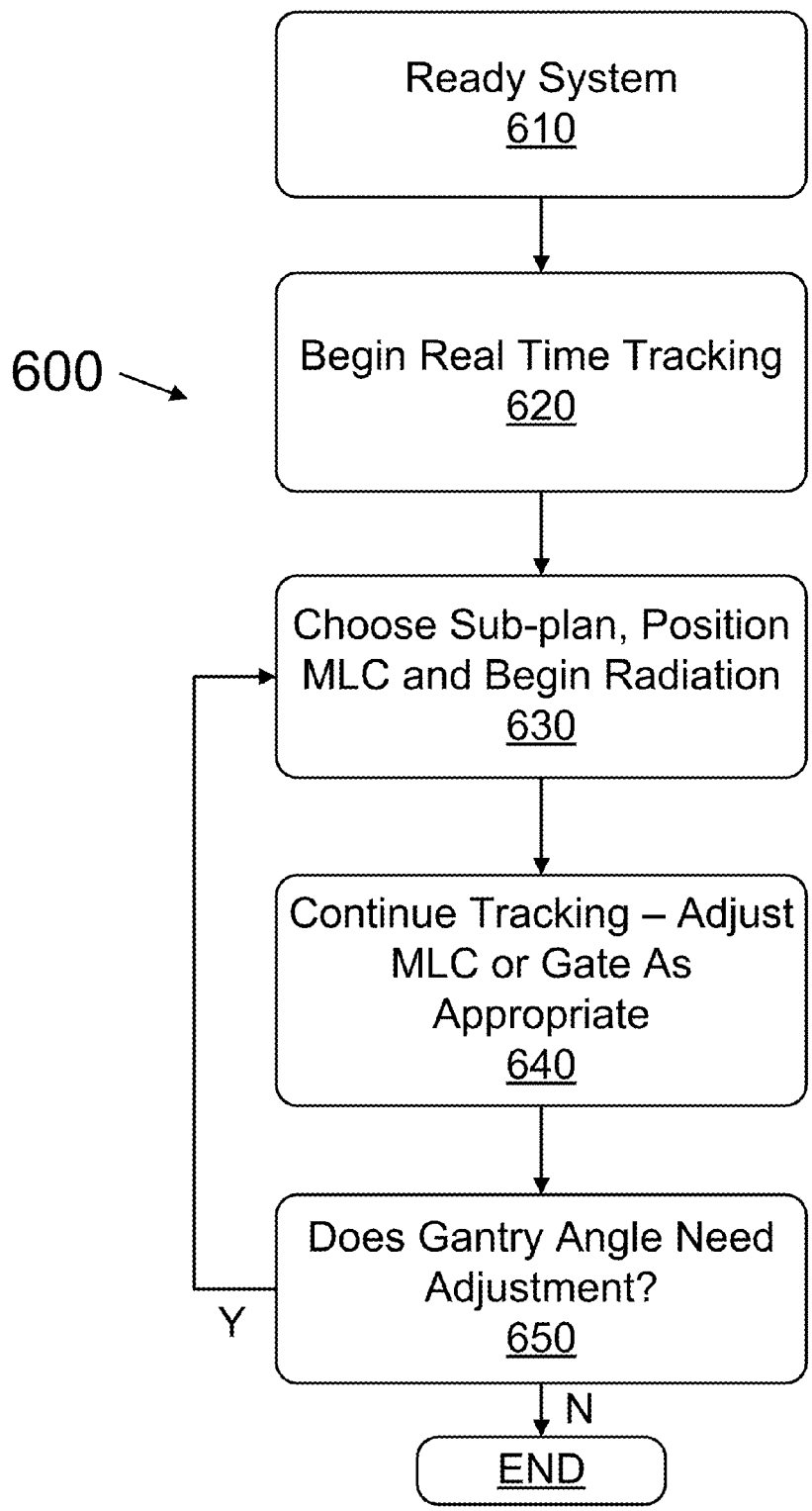
FIG. 6 is a flow chart depicting a method of treatment in accordance with an embodiment of the present invention.

FIG. 6 is a flow chart depicting a method of treatment 600 in accordance with an embodiment of the present invention. Prior to the commencement of treatment, the system is readied or initialized at step 610. This involves positioning the patient on the system table and performing any necessary preliminary imaging, positioning a tracking system for monitoring movements of the treatment volume, loading the treatment plan into the system, etc. Initializing the system may also include moving the gantry to the first angle that will be used for irradiating the patient. The treatment plan loaded into the system comprises a plurality of sub-plans as described above in connection with FIG. 5.

At step 620 the system begins tracking movements of the treatment volume in real time. The aforementioned '733 patent describes systems and techniques for target tracking. Based on position of the target, as determined at step 620, the system then selects the corresponding sub-plan, moves the MLC leaves into the proper position in real time, and begins delivering radiation in accordance with the selected sub-plan at step 630. At step 640, the system continues to track treatment volume movements in real time. When sufficient movement is detected the system either selects and implements the sub-plan corresponding to the new position by making appropriate adjustments to the MLC leaves in real time, or gates the system off (i.e., stops the radiation). It will be understood that the system may be gated off if the new position does not sufficiently correspond to one of the movement phases incorporated into the treatment plan. Generally, this will involve an unexpected movement rather than a predicted movement that was incorporated into the planning process. Once the tracking system determines that target position has returned to a predicted position, the system is gated back on and the appropriated sub-plan is implemented in real time. It will be further understood that in IMRT for any given sub-plan the leaves of the MLC will be moved to modulate the fluence delivered to different portions of the target. At step 650, after the prescribed fractional dose is delivered from a given gantry angle, the gantry may then be moved to another angle if called for in the treatment plan, and the process repeated. Once the prescribed fractional dose has been delivered from each angle called for in the treatment plan, the process ends.

The embodiments described above are illustrative of the present invention and are not intended to limit the scope of the invention to the particular embodiments described. Accordingly, while one or more embodiments of the invention have been illustrated and described, it will be appreciated that various changes can be made therein without departing from the spirit or essential characteristics thereof. Accordingly, the disclosures and descriptions herein are not intended to be limiting of the scope of the invention, which is set forth in the following claims.

What is claimed is:

1. A method of using a radiation therapy system to perform intensity modulated radiation therapy on a selected target volume within a patient, wherein the target volume undergoes generally predictable movements, the method comprising:
   delivering radiation in accordance with a treatment plan developed for the patient, wherein the treatment plan is developed using:
      a plurality of inputs comprising target volume movement data and anticipated target volume movement data, and
      one or more constraints comprising movement limitations of a multileaf collimator of the radiation therapy system;
   determining a target volume position and tracking target volume movement;
   determining a first position of leaves of the multileaf collimator for a first phase of the target volume movement based on a second anticipated position of the leaves of the multileaf collimator for a second phase of the target volume movement; and
   moving leaves of the multileaf collimator to adjust for target volume movement according to the treatment plan.

2. The method of claim 1, wherein the treatment plan is optimized to minimize interplay of the plurality of inputs and constraints, and wherein the treatment plan minimizes interplay between multileaf collimator movements and the target volume movement by accounting for the movement limitations of the multileaf collimator.

3. The method of claim 1, wherein said treatment plan comprises a plurality of sub-plans, at least some of said plurality of sub-plans corresponding to anticipated phases of the target volume movement, the method further comprising:
selecting a sub-plan from the plurality of sub-plans to implement based on the determined target volume position.

4. The method of claim 1, wherein an aperture defined by the leaves of the multileaf collimator is elongated in a direction that is generally parallel to the target volume movement.

5. The method of claim 1, wherein the one or more constraints involve at least one of fluence capabilities, gantry speed, and table movement.

6. A method of using a radiation therapy system to perform intensity modulated radiation therapy on a selected target volume within a patient, wherein the target volume undergoes generally predictable movements, the method comprising:
delivering radiation in accordance with a treatment plan developed for the patient,
wherein the treatment plan is developed using:
a plurality of inputs comprising target volume movement data and anticipated target volume movement data, and
one or more constraints comprising movement limitations of a multileaf collimator of the radiation therapy system, wherein said treatment plan comprises a plurality of sub-plans, at least some of said plurality of sub-plans corresponding to anticipated phases of target volume movement;
determining a target volume position and tracking the target volume movement;
selecting a sub-plan from the plurality of sub-plans to implement based on the determined target volume position; and
moving leaves of the multileaf collimator to adjust for target volume movement according to the treatment plan, wherein a first sub-plan for a first phase of the target volume movement is based on a predicted position of the target volume in a next phase after the first phase.

7. The method of claim 6, wherein the first sub-plan of the treatment plan is developed to minimize a transition of the leaves of the multileaf collimator from the first phase to the next phase.

8. The method of claim 6, further comprising:
using the first sub-plan to facilitate a variation of the leaves of the multileaf collimator from one target volume position to the predicted position of the target volume in the next phase after the first phase.

9. The method of claim 8, wherein the plurality of sub-plans of the treatment plan are developed to facilitate leaf movements to a predicted region including the next anticipated target volume position of the next phase.

10. A non-transitory computer readable medium comprising program instructions that can be executed on a computer system for radiotherapy treatment planning to develop a patient treatment plan for use with a radiotherapy treatment system having a multileaf collimator, the treatment plan including a plurality of sub-plans for phases of generally predictable movements of a target volume, the program instructions comprising:
receiving data concerning one or more constraints comprising movement limitations of a multileaf collimator of the radiotherapy treatment system;
receiving data concerning a plurality of target positions corresponding to phases of the movement of the target volume;
optimizing a first sub-plan of a first phase by:
establishing a predicted region corresponding to a next phase of the target volume movement; and
determining positions of leaves of the multileaf collimator during the first phase based on the predicted region, positions of the leaves of the multileaf collimator for the next phase, and the one or more constraints.

11. The computer readable medium of claim 10, further comprising:
optimizing each sub-plan of the plurality of sub-plans by:
establishing a predicted region corresponding to a next phase of target volume movement; and
determining positions of leaves of the multileaf collimator during the sub-plan phase based on the predicted region, positions of the leaves of the multileaf collimator for the next phase, and the one or more constraints.

12. The computer readable medium of claim 11, wherein the plurality of sub-plans are simultaneously optimized.

13. The computer readable medium of claim 12, wherein the plurality of sub-plans are optimized using constraints from all of the phases.

14. The computer readable medium of claim 12, wherein simultaneously optimizing the plurality of sub-plans includes:
iteratively optimizing the plurality of sub-plans based on positions of the leaves of the multileaf collimator for each sub-plan for the current iteration.

15. The computer readable medium of claim 12, wherein the fluences are about the same for each phase of movement of the target volume.

16. The computer readable medium of claim 12, wherein simultaneously optimizing the plurality of sub-plans includes:
identifying a plurality of goals of the optimization, wherein a first goal is to minimize interplay between multileaf collimator movements and the target volume movement, and a second goal is to provide a prescribed dose of radiation for delivering to the target volume.

17. The computer readable medium of claim 16, wherein the optimization uses different weights for the different goals.

18. The computer readable medium of claim 10, wherein optimizing the first sub-plan of the first phase further includes:
receiving data concerning a maximum dose of radiation for delivering to the target volume within a treatment volume during the first sub-plan;
receiving data concerning a minimum dose of radiation for delivering to the target volume within the treatment volume during the first sub-plan; and
determining positions of leaves of the multileaf collimator corresponding to a dose less than the maximum dose to facilitate a transition of the leaves to positions for the next phase.

19. A radiation therapy system to perform intensity modulated radiation therapy on a selected target volume within a patient, wherein the target volume undergoes generally predictable movements, the system comprising:
a beam generator for delivering radiation in accordance with a treatment plan developed for the patient, wherein the treatment plan is developed using:
a plurality of inputs comprising target volume movement data and anticipated target volume movement data, and
one or more constraints comprising movement limitations of a multileaf collimator of the radiation therapy system; and a computer system configured to:
- determine a target volume position and track target volume movement;
- determine a first position of leaves of the multileaf collimator for a first phase of the target volume movement based on a second anticipated position of the leaves of the multileaf collimator for a second phase of the target volume movement; and
- move leaves of the multileaf collimator to adjust for target volume movement according to the treatment plan.

* * * * *